United States Patent [19]

Batz et al.

[11] Patent Number: 4,737,458
[45] Date of Patent: Apr. 12, 1988

[54] AMINOPYRAZOLINONES, REAGENT CONTAINING THEM AND THE USE THEREOF IN THE ENZYMATIC DETERMINATON OF HYDROGEN PEROXIDE

[75] Inventors: Hans-Georg Batz, Tutzing; Rupert Herrmann, Weilheim; Joachim Siedel, Bernried, all of Fed. Rep. of Germany

[73] Assignee: Boehringer Mannheim GmbH, Mannheim, Fed. Rep. of Germany

[21] Appl. No.: 894,735

[22] Filed: Aug. 8, 1986

Related U.S. Application Data

[63] Continuation of Ser. No. 731,884, May 8, 1985, abandoned.

[30] Foreign Application Priority Data

Jun. 19, 1984 [DE] Fed. Rep. of Germany ....... 3422732

[51] Int. Cl.$^4$ ...................... C12Q 1/28; C07D 231/46
[52] U.S. Cl. ........................................ 435/28; 548/365
[58] Field of Search ........................... 548/365; 435/28

[56] References Cited

U.S. PATENT DOCUMENTS 3,617,167 11/1971 Berth et al. ........................... 424/62
4,394,512 7/1983 Batz ..................................... 548/365

OTHER PUBLICATIONS

Liebigs Ann. Chem., 1976, pp. 1380–1394.
Beilsteins Handbuch der Organischen Chemie, 1930–1959, pp. 3552–3553.

Primary Examiner—Henry R. Jiles
Assistant Examiner—Kurt G. Briscoe
Attorney, Agent, or Firm—Felfe & Lynch

[57] ABSTRACT

The present invention provides aminopyrazolinones of the general formula:

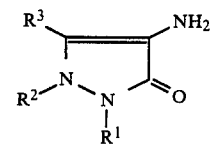

wherein $R^1$, $R^2$ and $R^3$, which can be the same or different, are straight-chained or branched alkyl radicals containing up to 6 carbon atoms and together containing at most 8 carbon atoms.

The present invention also provides a process for the preparation of these new aminopyrazolinones and reagents containing them. In addition, the present invention is concerned with the use of these new aminopyrazolinones as a color coupler for the detection of hydrogen peroxide.

9 Claims, No Drawings

AMINOPYRAZOLINONES, REAGENT CONTAINING THEM AND THE USE THEREOF IN THE ENZYMATIC DETERMINATON OF HYDROGEN PEROXIDE

This application is a continuation of application Ser. No. 731,884, filed May 8, 1985, now abandoned.

The present invention is concerned with new aminopyrazolinones, with the preparation thereof and with the use thereof as colour couplers for the detection of hydrogen peroxide in the presence of peroxidase and of a phenolic or anilinic coupling component.

The analytical determination of enzymatically formed hydrogen peroxide, for example of hydrogen peroxide formed by the oxidation of a serum component with oxygen and an oxidase, is of considerable importance for medical diagnosis. The amount of hydrogen peroxide formed, which is proportional to the amount of oxidase substrate present, can, for example, be determined enzymatically by reacting a chromogen in the presence of peroxidase with the hydrogen peroxide to give a photometrically determinable coloured material. The amount of coloured material formed serves as a measure of the hydrogen peroxide-forming substrate.

A known chromogen for the determination of hydrogen peroxide is Trinder's indicator system (see Ann. Clin. Biochemistry, 6, 24–27 (1969)) in the case of which a colour coupler (4-aminoantipyrine, 4-AAP) is oxidatively coupled with a coupling component (phenol) in the presence of peroxidase with the participation of hydrogen peroxide to give a coloured material. Instead of phenol, there can also be used other phenolic or anilinic compounds, the coloured materials formed with anilinic compounds, for example N-ethyl-N-hydroxyethyl-3-methylaniline (EHT; see Federal Republic of Germany Patent Specification No. 31 24 594) or N-ethyl-N-(3-methylphenyl)-N'-acetamidoethylenediamine (EMAE; see European Patent Specification No. 0007787) thereby displaying a comparatively high molar extinction coefficient at a wavelength maximum displaced bathochromically by about 50 nm. It follows from this, especially in the case of the determination of serum components present in low concentration, for example urea or creatinine, that it is advantageous to use anilinic coupling components rather than phenolic coupling components.

As colour couplers, there can be used, apart from 4-aminoantipyrine, also other aminoantipyrine derivatives (for example diaminoantipyrine, see Federal Republic of Germany Patent Specification No. 31 00 807), methylbenzthiazolone hydrazone (MBTH), sulphonated MBTH (SMBTH) and similarly reacting compounds. A disadvantage of all of these colour couplers in the case of the above-described determination of hydrogen peroxide is, besides the sometimes poor blank stability caused by autoxidation, the insufficient stability of the coloured material formed with the anilinic coupling component (see, for example, Federal Republic of Germany Patent Specification No. 31 24 549). An improvement of the colour stability would be of great practical advantage, for example by making possible longer reading off times.

Therefore, it is an object of the present invention to provide new compounds which do not suffer from the above-mentioned disadvantages and which can be used as colour formers in the determination of hydrogen peroxide instead of 4-aminoantipyrine or of other known colour couplers and which display a better colour stability of the coloured material formed by the oxidative coupling thereof with anilinic coupling components.

Thus, according to the present invention, there are provided new aminopyrazolinones of the general formula:

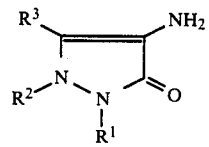

wherein $R^1$, $R^2$ and $R^3$, which can be the same or different, are straight-chained or branched alkyl radicals containing up to 6 carbon atoms and together containing at most 8 carbon atoms.

The new compounds according to the present invention can be prepared, for example, by nitrating or nitrosating the corresponding trialkylpyrazolinones by known methods and subsequently reducing the nitro or nitroso group with, for example, zinc/hydrochloric acid or hydrogen/catalyst. The trialkylpyrazolinones used as starting materials for this synthesis can also be obtained by known methods, for example by reacting 1,2-dialkylhydrazines with acylacetic acid esters or by alkylation of appropriate dialkylpyrazolinones. Such methods are described, for example, in W. Krohs, O. Hensel, Pyrazolone and Dioxopyrazolidine, Editio Cantor, Aulendorff/Württemberg, 1961, and R. H. Wiley and P. Wiley in A. Weissberger (ed.), Pyrazolones, Pyrazolidones and Derivatives, Interscience Publishers, New York, London and Sydney, 1964.

4-Amino-1,2,3-trimethylpyrazolin-5-one (TAP) is a preferred compound according to the present invention. Examples of other preferred compounds according to the present invention include 1,2,3-triethylpyrazolin-5-one, 1,2-dimethyl-3-isopropylpyrazolin-5-one, 1-n-butyl-2,3-diethylpyrazolin-5-one, 1-tert.-butyl-2,3-dimethylpyrazolin-5-one and 1-hexyl-2,3-dimethylpyrazolin-5-one and the like.

The present invention is also concerned with the use of the above compounds for the determination of hydrogen peroxide by an oxidative colour formation reaction with anilinic or phenolic components and peroxidase as colour coupler.

As anilinic coupling components, there are preferred N-ethyl-N-hydroxyethyl-3-methylaniline (EHT) and N-ethyl-N-(3-methylphenyl)-N'-acetamidoethylenediamine (EMAE). Other anilinic coupling components which can be used according to the present invention for colour formation include N-ethyl-N-(4-fluoro-3-methylphenyl)-N'-acetamidoethylenediamine (F-EMAE), N-ethyl-N-(2-sulphoethyl)-m-toluidine (EST), N-ethyl-N-(3'-sulphobenzyl)-m-toluidine, other aniline derivatives, naphthylamine, naphthylamine derivatives, aminoquinolines and the like.

The colour formation with the use of the preferred compound according to the present invention, i.e. 4-amino-1,2,3-trimethylpyrazolin-5-one (TAP), as colour coupler with EHT as anilinic coupling component is illustrated by the following reaction equation:

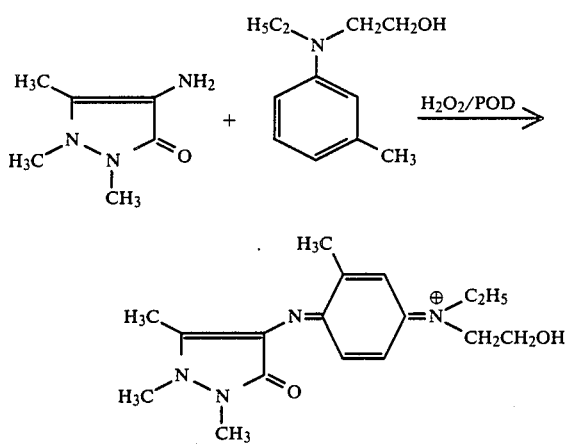

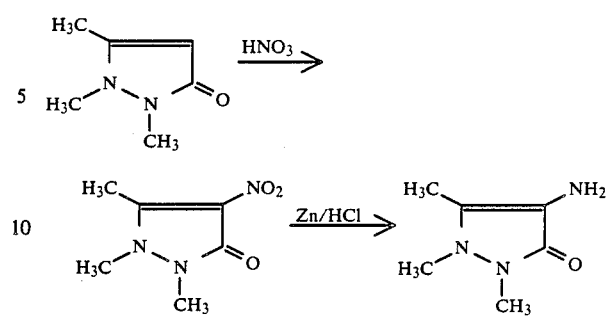

(a) 4-Nitro-1,2,3-trimethylpyrazolin-5-one.

1 g. 1,2,3-Trimethylpyrazolin-5-one monohydrate is added portionwise at 70° C. to 5.5 ml. concentrated nitric acid, the temperature thereby not being allowed to exceed 75° C. 30 Minutes after completion of the addition, the reaction mixture is evaporated in a vacuum and poured on to 10 g. of ice. The pH is adjusted to 7 with 5N aqueous sodium hydroxide solution, while cooling, and the crude product which thereby precipitates out is filtered off with suction. Further product can be obtained from the mother liquor by evaporation. The crude nitropyrazolinone compound obtained can be purified by recrystallisation from water/isopropanol. Yield: 0.96 g. (71% of theory).

$^1$H-NMR (DMSO-D$_6$): δ=260 (s, 3H); 3.36 (s, 3H); 3.65 ppm (s, 3H).

Elementary analysis: C$_6$H$_9$N$_3$O$_3$ (M.W. 171.16). calc.: C, 42.11%; H, 5.30%; N, 24.55%. found: C, 42.2%; H, 5.42%; N, 25.18%.

(b) 4-Amino-1,2,3-trimethylpyrazolin-5-one.

A solution of 2.8 g. 4-nitro-1,2,3-trimethylpyrazolin-5-one in 8.4 ml. concentrated hydrochloric acid and 3 ml. water is added dropwise, with cooling, to a suspension of 6.4 g. zinc dust in 5 ml. water, the reaction temperature thereby being kept between 25° and 30° C. The reaction mixture is then further stirred for 2 hours at 60° C., whereafter the reaction mixture is poured on to ice and rendered alkaline with 5N aqueous sodium hydroxide solution. The precipitated zinc salts are filtered off with suction, the mother liquor is substantially evaporated and the residue is shaken out several times with chloroform. After drying the organic phase over anhydrous sodium sulphate, it is evaporated in a vacuum, the desired product thereby crystallising. Yield: 0.93 g. (40% of theory).

$^1$H-NMR (DMSO-D$_6$): δ=1.98 (s, 3H); 2.85 (s, 3H); 3.11 (s, 3H); 3.63 ppm (s, br, 2H).

Elementary analysis: C$_6$H$_{11}$N$_3$O (M.W. 141.17). calc.: C, 51.09%; H, 7.85%; N, 29.76%. found: C, 49.56%; H, 7.93%; N, 28.9%.

EXAMPLE 2

This Example illustrates the colour stabilities in the case of the oxidative coupling of various coupling components with TAP, as well as with 4-AAP as comparative substance.

The colour formation of the compounds according to the present invention with, for example, phenolic compounds also takes place analogously to the above equation. In principle, all compounds which are used as coupling components in the case of the oxidative colour formation reaction with conventional couplers can also be used with the couplers according to the present invention.

Examples of other conventional coupling compounds which are not anilinic coupling components and which, together with the compounds according to the present invention, can be used for the colour formation in the scope of the detection of hydrogen peroxide include, for example, phenol, 4-chlorophenol, other phenol derivatives, naphthol, naphthol derivatives, hydroxyquinolines, dihydroxyphenylacetic acid and the like.

The reaction in the case of the coloured material formation is carried out in a buffered solution. As buffer substances and pH values, there can be used the conditions known in this regard for peroxidase, pH values of from 5 to 9 being preferred. In addition, the choice of the buffer and of the pH value in the case of a preceding hydrogen peroxide-forming enzymatic reaction is, in particular, dictated by the requirements with regard to the buffer and pH value of the enzymes participating therein. All these conditions are well known to the expert and, therefore, do not require a detailed explanation.

A reagent for the determination of hydrogen peroxide based on peroxidase, at least one of the compounds according to the present invention, at least one coupling component and buffer substance can, in addition, also contain conventional solvents, stabilisers and/or surface-active substances. The following amount ratios of the essential components of this reagent have proved to be especially useful:

0.1 to 100 U/ml. of peroxidase
0.01 to 20 mMol/liter of compound according to the present invention
0.1 to 50 mMol/liter of coupling component.

Surface-active agents, when they are present, are preferably used in amounts of from 0.001 to 0.1 g./ml., referred to the reagent solution ready for use.

The following Examples are given for the purpose of illustrating the present invention:

EXAMPLE 1

Preparation of 4-amino-1,2,3-trimethylpyrazolin-5-one (TAP).

| Concentrations in the test batch: | |
| --- | --- |
| potassium phosphate buffer (pH 7.0) | 0.1 mol/liter |
| colour coupler | 3 × 10$^{-2}$ mmol/liter |
| coupling component | 3 × 10$^{-1}$ mmol/liter |
| Triton X 100 | 5 mg./ml. |
| peroxidase | 1.2 μ/ml. |

| -continued |  |
|---|---|
| Concentrations in the test batch: |  |
| hydrogen peroxide | $1.5 \times 10^{-2}$ mmol/liter |

Buffer is present in a comparison cuvette. The measurement wavelength in the case of the determination of the colour stability is 550 nm, and the temperature is 25° C. The course of the extinction is monitored for 12 hours, the measurements being carried out hourly.

The statement of the colour stability is expressed as a percentage and refers to the deviation of the measurement signal at the time in question from the initial measurement signal which was determined 2 minutes after the addition of the hydrogen peroxide.

The results obtained are summarised in the following Table, together with the $\lambda_{max}$ and $\epsilon$ values of the initial material.

TABLE

| coupling component colour | EHT | | EMAE | | F-EMAE | |
|---|---|---|---|---|---|---|
| coupler | TAP | 4-AAP | TAP | 4-AAP | TAP | 4-AAP |
| $\lambda_{max}(nm)$ | 552 | 550 | 555 | 552 | 556 | 552 |
| $\epsilon(cm^2/mol\ H_2O_2)$ | 14.4 | 14.7 | 15.4 | 15.9 | 29.5 | 27.8 |
| colour stability in % after | | | | | | |
| 1 h. | 0.0 | −0.2 | 0.0 | −0.2 | −0.6 | −2.1 |
| 2 h. | −0.2 | −0.3 | −0.5 | −0.9 | −1.0 | −3.3 |
| 6 h. | −1.4 | −5.5 | −1.2 | −6.6 | −2.2 | −9.6 |
| 12 h. | −5.6 | −13.6 | −3.9 | −15.7 | −5.1 | −17.9 |

We claim:

1. An aminopyrazolinone of the formula:

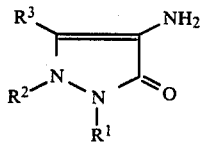

wherein $R_1$ is $C_1$–$C_6$ alkyl,
$R_2$ is $C_1$–$C_6$ alkyl and
$R_3$ is $C_1$–$C_6$ alkyl,
with the proviso that $R^1$, $R^2$ and $R^3$ together total 3 to 8 carbon atoms.

2. 4-Amino-1,2,3-trimethylpyrazolin-5-one.

3. The aminopyrazolinone of claim 1 wherein $R^1=R^2=R^3$.

4. The aminopyrazolinone of claim 1 wherein $R^2=R^3$.

5. The aminopyrazolinone of claim 1 wherein $R^2=R^3=$methyl or ethyl.

6. The aminopyrazolinone of claim 1 designated 1,2,3-triethyl-pyrazolin-5-one, 1,2-dimethyl-3-isopropylpyrazolin-5-one, 1-n-butyl-2,3-diethylpyrazolin-5-one, 1-tert-butyl-2,3-dimethyl-pyrazolin-5-one or 1-hexyl-2,3-dimethylpyrazolin-5-one.

7. In a method of detection of hydrogen peroxide the improvement wherein, an aminopyrazolinone of the formula:

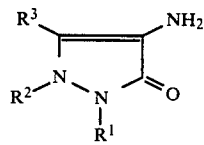

wherein $R_1$ is $C_1$–$C_6$ alkyl, $R_2$ is $C_1$–$C_6$ alkyl and $R_3$ is $C_1$–$C_6$ alkyl, with the proviso that $R^1$, $R^2$ and $R^3$ together total 3 to 8 carbon atoms, is used as a colour coupler for the detection of hydrogen peroxide in the presence of peroxidase, with a phenolic or anilinic coupling component.

8. The method according to claim 7, wherein the coupling component is an anilinic coupling component selected from N-ethyl-N-hydroxyethyl-3-methylaniline and N-ethyl-N-(3-methylphenyl)-N'-acetamidoethylenediamine.

9. A reagent for the determination of hydrogen peroxide, containing peroxidase, at least one compound according to claim 1, at least one coupling component and a buffer.

* * * * *